(12) United States Patent
Nobuki et al.

(10) Patent No.: US 10,302,641 B2
(45) Date of Patent: May 28, 2019

(54) AUTOMATIC ANALYSIS DEVICE

(71) Applicants: Shunichiro Nobuki, Tokyo (JP);
Muneo Maeshima, Tokyo (JP); Terumi Tamura, Tokyo (JP); Kenta Imai, Tokyo (JP)

(72) Inventors: Shunichiro Nobuki, Tokyo (JP);
Muneo Maeshima, Tokyo (JP); Terumi Tamura, Tokyo (JP); Kenta Imai, Tokyo (JP)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 439 days.

(21) Appl. No.: 14/766,377

(22) PCT Filed: Jan. 23, 2014

(86) PCT No.: PCT/JP2014/051321
§ 371 (c)(1),
(2) Date: Nov. 20, 2015

(87) PCT Pub. No.: WO2014/122996
PCT Pub. Date: Aug. 14, 2014

(65) Prior Publication Data
US 2016/0061831 A1     Mar. 3, 2016

(30) Foreign Application Priority Data
Feb. 8, 2013  (JP) .................................. 2013-022799

(51) Int. Cl.
*G01N 21/05*    (2006.01)
*G01N 21/69*    (2006.01)
(Continued)

(52) U.S. Cl.
CPC ............ *G01N 33/561* (2013.01); *G01N 21/05* (2013.01); *G01N 21/69* (2013.01); *G01N 21/76* (2013.01);
(Continued)

(58) Field of Classification Search
CPC ........... G01N 33/561; G01N 33/54326; G01N 21/05; G01N 21/69; G01N 21/76; G01N 21/745; G01N 35/0098
See application file for complete search history.

(56) References Cited

U.S. PATENT DOCUMENTS 4,619,745 A   10/1986 Porta et al.
5,061,445 A   10/1991 Zoski et al.
(Continued)

FOREIGN PATENT DOCUMENTS

CN    101957338 A    1/2011
CN    102010035 A    4/2011
(Continued)

OTHER PUBLICATIONS

International Search Report and Written Opinion dated Mar. 18, 2014 pertaining to PCT Application No. PCT/JP2014/051321.
(Continued)

*Primary Examiner* — Robert J Eom
(74) *Attorney, Agent, or Firm* — Dinsmore & Shohl LLP

(57) ABSTRACT

An analyzing device of the present invention is provided with a flow chamber that a fluid including magnetic particles associated with a labeling substance flows from a fluid inlet to a fluid outlet, magnetic trap means to apply a magnetic field for trapping the magnetic particles to the fluid in the flow chamber, a working electrode and a counter electrode to apply a voltage to the magnetic particles trapped by the magnetic trap means, and to emit a luminescence, a light detection element to detect a luminescence derived from the
(Continued)

labeling substance on the magnetic particles trapped in the flow chamber, and regulating means to regulate a region that the light detection element detects the luminescence derived from the labeling substance on a part of magnetic particles of them trapped by the magnetic trap means.

16 Claims, 6 Drawing Sheets

(51) Int. Cl.
  *G01N 21/76* (2006.01)
  *G01N 27/74* (2006.01)
  *G01N 35/00* (2006.01)
  *G01N 33/543* (2006.01)
  *G01N 33/561* (2006.01)

(52) U.S. Cl.
  CPC ..... *G01N 27/745* (2013.01); *G01N 33/54326* (2013.01); *G01N 35/0098* (2013.01)

(56) References Cited

U.S. PATENT DOCUMENTS

| | | | |
|---|---|---|---|
| 5,744,367 A | 4/1998 | Talley et al. | |
| 5,993,740 A | 11/1999 | Niiyama et al. | |
| 6,133,043 A | 10/2000 | Talley et al. | |
| 2004/0090168 A1* | 5/2004 | Kumar | G01N 21/69 313/483 |
| 2008/0047332 A1 | 2/2008 | Kuhnl et al. | |
| 2010/0228513 A1 | 9/2010 | Roth et al. | |
| 2012/0252138 A1 | 10/2012 | Sasso, Jr. et al. | |
| 2013/0143234 A1 | 6/2013 | Inaba et al. | |

FOREIGN PATENT DOCUMENTS

| | | |
|---|---|---|
| CN | 102095771 A | 6/2011 |
| JP | 4-502207 | 4/1992 |
| JP | 08-146002 | 6/1996 |
| JP | 10-221342 | 8/1998 |
| JP | 10-509798 | 9/1998 |
| JP | 10-332593 | 12/1998 |
| JP | 11-118706 | 4/1999 |
| JP | 11-242032 | 9/1999 |
| JP | 2000-065833 | 3/2000 |
| JP | 2008-51813 | 3/2008 |
| WO | 96/15440 A1 | 5/1996 |
| WO | 99/58962 A1 | 11/1999 |
| WO | 2004/001380 A2 | 12/2003 |
| WO | 2011/155489 A1 | 12/2011 |

OTHER PUBLICATIONS

Extended European Search Report dated Feb. 11, 2016 pertaining to US Patent Application No. 14749616.0-1554 / 2955508 and PCT Application No. PCT/JP2014/051321.

Chinese Patent Office, Office Action dated Mar. 24, 2017 in reference to co-pending Chinese Patent Application 201480007866.3 filed Jan. 23, 2014.

* cited by examiner

AUTOMATIC ANALYSIS DEVICE

TECHNICAL FIELD

The present invention relates to a device for immunity analysis (immunoassay) using a reaction between an antigen and an antibody, and more particularly, to an analyzing device using magnetic particles as a solid phase for immunity reaction.

BACKGROUND ART

An immunity reaction is used to form an immunity complex for identifying an antibody or antigen in a biological sample such as serum or urine. When a solid phase and a liquid phase are made to react with each other, it is a general practice that a labeled antibody is used as a reagent and the liquid phase is measured using a detection element after the reaction. Radioisotopes, enzymes, colored particles, fluorescent substances, light-emitting (luminescent) substances or the like are known as the labeling substances.

In electrochemical luminescent flow-through cells according to prior arts, an excessive amount of luminescent reagent is added with respect to an amount of a measuring target in order to cause the luminescent reagent to be bound to a trace amount of the measuring target with a high probability, and therefore a large amount of the luminescent reagent (free component) which is not bound to the measuring target exists in a solution, resulting in a problem that a noise signal originating from the free component causes an SN ratio to deteriorate.

As a prior art, Patent Literature 1 discloses the following technique. That is, the patent literature includes a description that a magnet is placed outside a wall surface of a flow-through cell, a measuring target (hormone, tumor marker, drug, enzyme, cytokine, nucleic acid or the like) is held to magnetic beads via an antigen-antibody bond, the magnetic beads are held to the surface of a working electrode via a magnet, and a component which is not held to the surface of the working electrode and which is a noise originating component is washed away by the force of water flow to improve measuring accuracy. Separation between the component held to the surface of the working electrode (binding component (Bind; B)) and the component not held to the surface of the working electrode (free component (Free; F)) is called "B/F separation."

CITATION LIST

Patent Literature

Patent Literature 1: National Publication of International Patent Application No. 1992-502207

SUMMARY OF INVENTION

Technical Problem

However, the configuration described in Patent Literature 1 cannot remove unnecessary luminescence originating from electrochemical reaction between an attractant (TPA or the like, which will be described later) that excites a labeling substance which is not directly bound to the measuring target and the working electrode. In the case of a region where a density of magnetic particles on the surface of the working electrode is relatively small in particular, a ratio of unnecessary luminescence caused by the attractant (TPA or the like) that excites the labeling substance is large relative to a target ratio of luminescence emitted from the luminescent label and the region becomes a region where the SN ratio is locally (relatively) low. For this reason, it is difficult to obtain a high SN ratio.

It is an object of the present invention to reduce such regions where the density of magnetic particles on the surface of the working electrode is relatively small, and thereby reduce regions where the SN ratio is locally (relatively) low and obtain a high SN ratio.

Solution to Problem

Features of the present invention to solve the above-described problems are as follows.

An analyzing device of the present invention includes a flow chamber through which a fluid containing magnetic particles flows, a flow-through cell including the flow chamber, a working electrode and a counter electrode provided in the flow chamber, a magnet that applies a magnetic field for trapping the magnetic particles in the flow chamber when the fluid containing the magnetic particles is introduced into the flow chamber, and a photodetection element that detects luminescence emitted from a labeling substance on the magnetic particles remaining in the flow chamber, in which an area of an exposed region of the working electrode in the flow chamber is smaller than an area of a top part of the magnet.

Advantageous Effects of Invention

The method and device for immunity analysis using magnetic particles according to the present invention reduces a photometric amount from a region where a density of magnetic particles on the surface of the working electrode is relatively small, and can thereby reduce regions where an SN ratio is locally (relatively) low and obtain a high SN ratio. The problems, configuration and effects other than those described above will be made clear in the description of the following embodiments.

DESCRIPTION OF EMBODIMENTS

Figure 1:
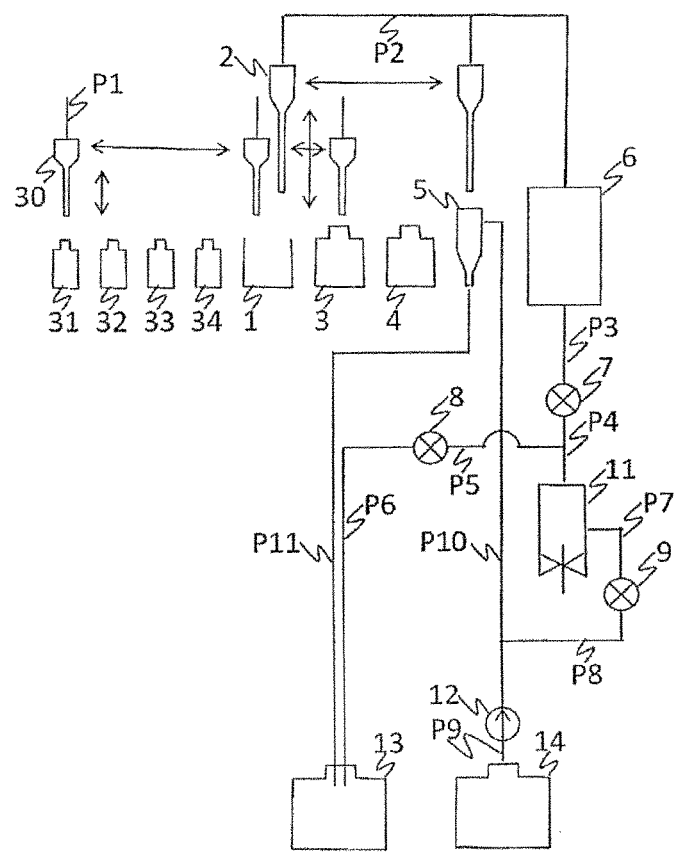
FIG. 1 is a diagram illustrating an overall schematic configuration of an immunity analyzing device according to an embodiment of the present invention.

When a sample is serum, examples of components to be analyzed (analysis target) include antigen, peptide hormone, steroid hormone, drug, virus antibody, various tumor markers, antibody, antibody complex, single protein or the like.

Magnetic particles as a solid phase have a particle size of 0.5 to 10 µm and have a specific gravity of 1.2 to 1.5. These particles hardly precipitate into a liquid and are likely to be suspended. An antibody is fixed to the surface of particles. The magnetic particles are formed by embedding powder of a magnetic attractant such as iron, iron oxide, nickel, cobalt, chromium oxide into a matrix and this matrix itself is made of a wide range of substances including many synthetic and natural polymerizable substances (e.g., cellulose, polyester, polystyrene, silica, dextran, albumin).

Through an immunity reaction, an immunity complex including an analysis target (antigen) and a luminescent labeling substance is bound on magnetic particles. This immunity complex is introduced into a flow chamber of the flow-through cell in the form of suspension together with other coexisting substances in the reaction compound.

The magnetic particles are planarly spread in the flow chamber and trapped in a predetermined place by a magnetic force. The magnetic force is canceled when luminescence is measured, but since the flow of the liquid in the flow chamber is stopped, the magnetic particles remain trapped in the flow chamber.

The flow chamber is formed such that the width thereof is 2 to 20 times the depth thereof (that is, thickness), making it easier for particles introduced on the flow of the fluid to spread in the lateral direction of the flow. Ideally, the magnetic particles preferably spread in a single layer, but overlapping among particles actually occurs in some degree. In the present invention, the case where such overlapping occurs is also called "planar spreading." The planar spreading in the flow chamber is influenced not only by the magnitude of the magnetic force but also the flow rate when a suspension including a reaction compound is introduced. When a force by the flow rate exceeds a force of trapping particles by a magnetic force, particles are separated, and so it is necessary to select an appropriate flow rate.

The magnetic flux density of a magnet for applying a magnetic field to the flow chamber is preferably 0.5 to 3 T. The flow-through cell includes a light transmissive window between the flow chamber and a photodetection element. The window is made of any one material selected from among plastic having an internal light transmissivity of 90% or higher such as glass, quartz, acrylic, polycarbonate. The photodetection element is any one selected from among a photomultiplier tube, avalanche photodiode, photodiode, streak tube. The window may have a convex lens shape.

In the flow-through cell, a reaction product is separated from the liquid phase of the suspension in the flow chamber in the flow-through cell placed at a predetermined position in a channel using magnetic trap means. The suspension is guided to the flow chamber in the flow-through cell by liquid feeding means made up of means for suctioning or discharging the suspension along the channel, and when the suspension reaches a region of a local magnetic field by the magnet arranged below or above a working electrode, the suspension is trapped on the working electrode by a magnetic force thereof.

Conditions required in the process of introducing the suspension into the flow chamber in the flow-through cell and trapping reaction products on the working electrode are as follows. That is, the region where the density of magnetic particles on the surface of the working electrode is relatively small is reduced in order to increase the sensitivity (SN ratio) of luminescence by the labeling substance. In the region where the density of magnetic particles on the surface of the working electrode is relatively small, the ratio of unnecessary luminescence due to an attractant (TPA or the like) that excites the labeling substance is large relative to the ratio of luminescence emitted from the target luminescent label and the region becomes a region where the SN ratio is locally (relatively) low. For this reason, it is difficult to obtain a high SN ratio, which is therefore not desirable.

The shape of the flow chamber is a spindle shape when seen from the top surface and the flow chamber has a structure in which the width of the maximum width portion of the spindle shape is within ten times the inlet diameter (minimum width portion), the angle of aperture with respect to the maximum width portion when seen from the inlet is within 30° and the thickness thereof is 0.2 to 1.0 mm. In the case of an inappropriate shape, separation of the flow in the vicinity of the chamber side face or retention of bubbles is more likely to occur, which may prevent trapping of the reaction product in the suspension to the working electrode, prevent a cleaning liquid from wrapping around to the side face portion of the flow chamber when cleaning the once trapped reaction product and thereby make it difficult to clean the reaction product after a luminescent reaction.

In order to prevent adherence of dirt deriving from a protein component or the like in the sample and prevent deterioration due to a cleaning liquid as much as possible, the material of the flow chamber is selected from among fluororesin such as polytetrafluoroethylene, electric non-conductive substance such as butyl rubber, silicon rubber, glass, and acrylic resin.

In the case where the particle size of magnetic particles is 0.75 to 3 µm, when a suspension including a reaction product is introduced into the flow chamber, the flow condition can be optimized by setting a linear velocity thereof to 10 to 100 mm/s and more reaction products can be scattered and trapped on the working electrode. When the linear velocity is equal to or less than 10 mm/s, the reaction product in the suspension is trapped concentrated on one point on the working electrode, and it is therefore more difficult to secure high luminescence efficiency when performing electrochemical luminescence. Moreover, when the linear velocity is equal to or greater than 100 mm/s, the reaction product is less likely to be trapped on the working electrode, most parts thereof are carried off, causing the amount of luminescence to decrease.

The solid phase made up of the reaction product trapped on the working electrode when the suspension passes through the flow chamber in the flow-through cell can be cleaned by causing a cleaning liquid to flow into the flow chamber via the channel. The solid phase remains trapped on the working electrode, but the reaction product is exposed to the flowing cleaning liquid and thereby cleaned.

The cleaning liquid is preferably a buffer solution containing an attractant that excites the labeling substance when a luminescent reaction in the subsequent process is taken into consideration. Purposes of the use of the buffer solution include erasing traces of the suspension liquid phase from the solid phase and supplying a substance that induces excitation of the labeling substance around the reaction product with high reproducibility.

The magnetic particles are trapped through a local magnetic trap caused by a magnet placed on the working electrode when the working electrode is placed on the top surface of the flow chamber or a magnet placed below the working electrode in the opposite case. The working electrode may be arranged on either the top surface or the undersurface of the flow chamber, but the working electrode is preferably arranged on the undersurface when the trapping efficiency and ease of arrangement are taken into consideration and is preferably arranged in the vicinity of the spindle-shaped maximum width portion.

Here, the "area of an exposed region of the working electrode in the flow chamber" is preferably smaller than the "area of a top part of the magnet" and is further preferably equal to or less than ⅔ of the "area of a top part of the magnet," or further preferably equal to or less than ⅓ of the "area of a top part of the magnet" for improving the SN ratio of the device. The reasons are as follows. That is, the number density of magnetic particles is determined by a magnetic flux density (and flow rate or the like) of the magnet. The magnetic flux density of the magnet generally has a spatial distribution, and so the number density of magnetic particles is not uniform, the region of approximately ⅔ of the size of the magnet has a large magnetic flux density, a region where there is a high concentration of magnetic particles is formed, the magnetic flux density is particularly large in approximately ⅓ of regions and the number density of magnetic particles is particularly high. Therefore, it is preferable to determine the area of the exposed region of the working electrode in the flow chamber as described in the foregoing paragraph.

On the other hand, in order to keep a number of magnetic particles effective for detecting a concentration of a specimen, the area of the exposed region of the working electrode in the flow chamber is preferably equal to or greater than 1% of the area of the top part of the magnet and further preferably equal to or greater than 5% of the area of the top part of the magnet.

Note that the "top part" of the magnet is the top part itself when part of the magnet opposing the flow chamber is flat, or an apparent region of the magnet when the top part is not flat, for example, when the top part includes irregularity parts or stepped parts.

Furthermore, the centroid of the "exposed region of the working electrode in the flow chamber" is preferably located in the upstream side in the flow chamber inside from the centroid of the top part of the magnet. This is because magnetic particles that flow through the flow chamber are first trapped on the upstream side corresponding to the edge of the magnet where the magnetic flux density is particularly large, and therefore the number density of magnetic particles is generally higher on the upstream side than the downstream side. Here, the "centroid" in the present specification refers to an average position within a two-dimensional plane of a specified region when the density is assumed to be uniform.

A basic shape of the "exposed region of the working electrode in the flow chamber" is selected from among a circle, ellipse and rectangle according to the shape of the magnet. Moreover, the shape of the "exposed region of the working electrode in the flow chamber" preferably includes a downstream-side emarginated part on the downstream side in the flow chamber in addition to the above-described basic shape. This is because the flow rate is particularly large in a central part of the channel of the flow chamber, and on the other hand, the flow rate is small in the vicinity of the wall surface, and the region where the number density of magnetic particles is high is likely to be smaller in the central part of the channel than in the vicinity of the wall surface. In this case, if the number of suction ports of the flow chamber is one, one downstream-side emarginated part in the center of the channel can sufficiently realize luminescence with a high SN ratio by reflecting the number density distribution of magnetic particles. On the other hand, in the case where there are two or more suction ports in the flow chamber, a plurality of downstream-side emarginated parts may be placed in accordance with an actual concentration distribution of magnetic particles and it is preferable to provide the same number of downstream-side emarginated parts as the suction ports.

Moreover, the "exposed region of the working electrode in the flow chamber" preferably includes upstream-side emarginated parts at both ends of the upstream side in the flow chamber. This is because when the magnet is placed below the working electrode, the central part of the channel of the flow chamber generally has a slightly higher magnetic flux density than in the vicinity of the wall surface, and so the region with a high number density of magnetic particles comes more on the upstream side of the flow in the central part of the channel than in the vicinity of the wall surface. On the other hand, in the vicinity of the wall surface, the region with a high number density of magnetic particles comes more on the downstream side of the flow.

In this case, since two wall surfaces exist on the left and right when seen from the flow direction, it is preferable to include upstream-side emarginated parts on both sides (both ends of the "exposed region of the working electrode in the flow chamber").

Furthermore, the "exposed region of the working electrode in the flow chamber" may be divided into an upstream-side working electrode exposed region located on the upstream side in the flow chamber and a downstream-side working electrode exposed region located on the downstream side in the flow chamber. This is because regions having a large magnetic flux density are generated on the upstream side and the downstream side of the flow originating from the fact that the magnetic flux density in the vicinity of the edge of the magnet is greater than other regions. Therefore, first of all, as has already been described, the working electrode is preferably formed on the upstream side (so that the centroid of the "exposed region of the working electrode in the flow chamber" in the upstream side in the flow chamber inside from the centroid of the "top part of the magnet"). That is, the centroid of the upstream-side working electrode exposed region is preferably located in the upstream side in the flow chamber inside from the centroid of the top part of the magnet. On the other hand, providing the working electrode also on the downstream side can efficiently trap magnetic particles in this region as well, and therefore the centroid of the downstream-side working electrode exposed region is preferably located in the downstream side in the flow chamber inside from the centroid at the top part of the magnet. Such a configuration can improve luminescence intensity without significantly reducing the SN ratio.

Any one of gold, platinum, palladium, tungsten, iridium, nickel and an alloy thereof is selected as the material of the working electrode and the counter electrode. This is intended to prevent wear of the surface caused by electrode reaction or corrosion by each reagent flowed on the electrode as much as possible.

The counter electrode and the working electrode are arranged on the same plane or at positions opposite to each other in the flow chamber.

A local magnetic trap is generated by at least one magnet placed on a side opposite to the flow chamber in the flow-through cell across the working electrode. This magnet can preferably approach a position of up to 0.5 to 3 mm from the surface of the working electrode and change the magnetic field from a minimum value to a maximum value as required. The magnetic field is changed, in the case where a permanent magnet is used, by moving the magnet away from or approaching the magnet to the plane of the working electrode so as to prevent generation of a magnetic field or, in the case where an electromagnet is used, by demagnetizing or exciting the electromagnet. For a reaction product bound to magnetic particles trapped on the working electrode, it is thereby possible to efficiently clean the reaction product remaining on the working electrode after completion of electrochemical luminescent reaction. Furthermore, by assuming the magnetic flux density of the magnet to be 0.5 to 3 T and arranging the magnet so that the distance from the surface of the working electrode may be reduced to 0.5 to 3 mm, it is possible to give a locally optimum magnetic field to the reaction product in the suspension that flows through the flow chamber via the channel, and thereby trap more reaction products in the suspension with high reproducibility, uniformly and with a wide range distribution.

After trapping the reaction product on the surface of the working electrode, by causing a buffer solution to flow into the flow chamber under this condition, it is possible to wash away the unreacted reagent more swiftly and with high efficiency and thereby simply perform B/F separation that minimizes carry-over.

The reaction product trapped on the working electrode is cleaned using the buffer solution, separated from an unreacted liquid phase, and with an attractant for exciting a labeling substance contained in the buffer solution being reduced by a voltage following a constant sequence applied between the working electrode and the counter electrode, light having a predetermined wavelength is emitted when the labeling substance excited by the reduced attractant transitions to a ground state. The light enters a transparent window provided at a position opposite to the working electrode across the flow chamber in the flow-through cell, introduced into a detection section of a photodetection element placed in contact with this window (or at a certain distance depending on the case) and luminescence intensity thereof is measured.

The flow-through cell having the above-described structure can analyze a specific component in a biological liquid sample such as serum, urine using a more rapid and simple method with high sensitivity and high reproducibility.

Hereinafter, embodiments of the present invention will be described with reference to the accompanying drawings. The following embodiments illustrate specific examples of contents of the present invention, and the present invention is not limited to these embodiments, but various changes and modifications can be made by those skilled in the art without departing from the scope of technological thought disclosed in the present specification. In all drawings for describing the embodiments, components having identical functions are assigned identical reference numerals and duplicate description thereof will be omitted.

Figure 2:
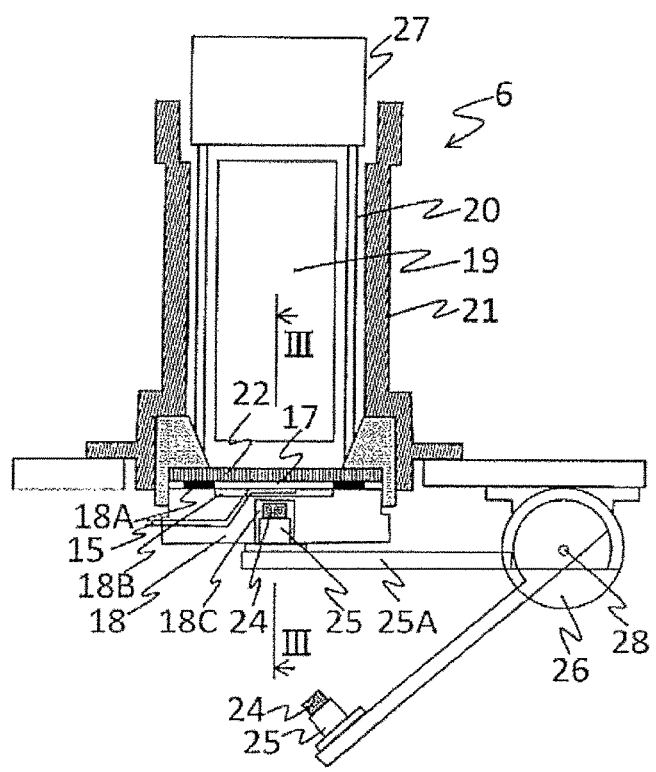
FIG. 2 is a longitudinal cross-sectional view illustrating a configuration of a flow-through cell unit in the device shown in FIG. 1.
Figure 3:
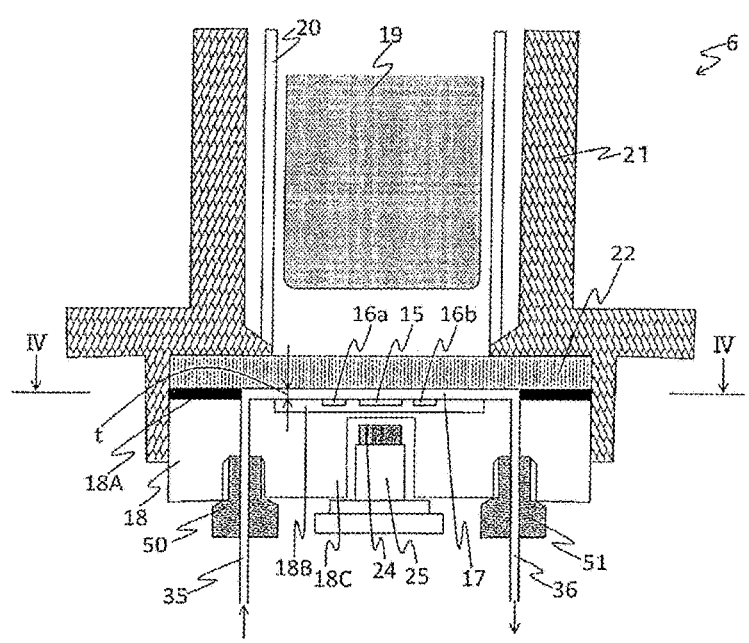
FIG. 3 is an enlarged view of a line III-III portion of the flow-through cell unit in FIG. 2.
Figure 4:
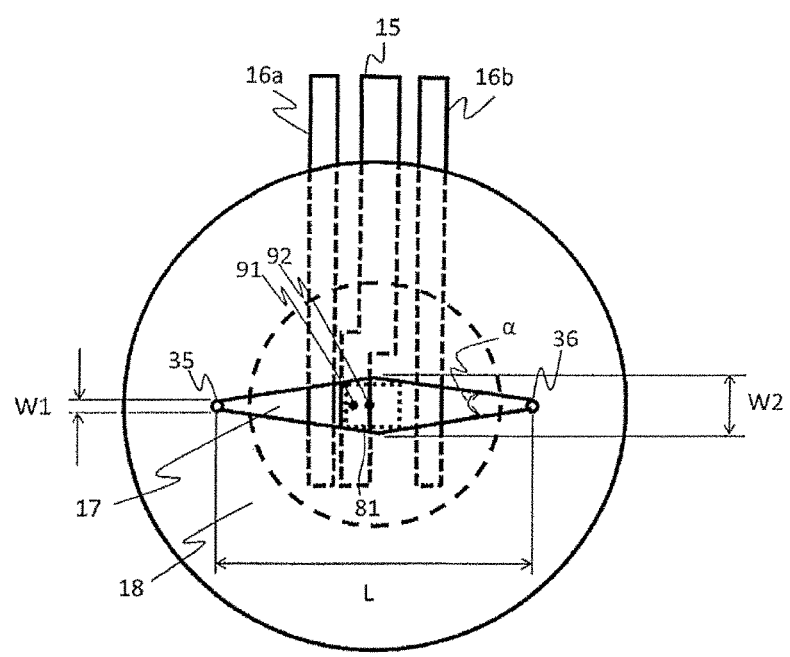
FIG. 4 is a cross-sectional view along a line IV-IV in FIG. 3.
Figure 5:
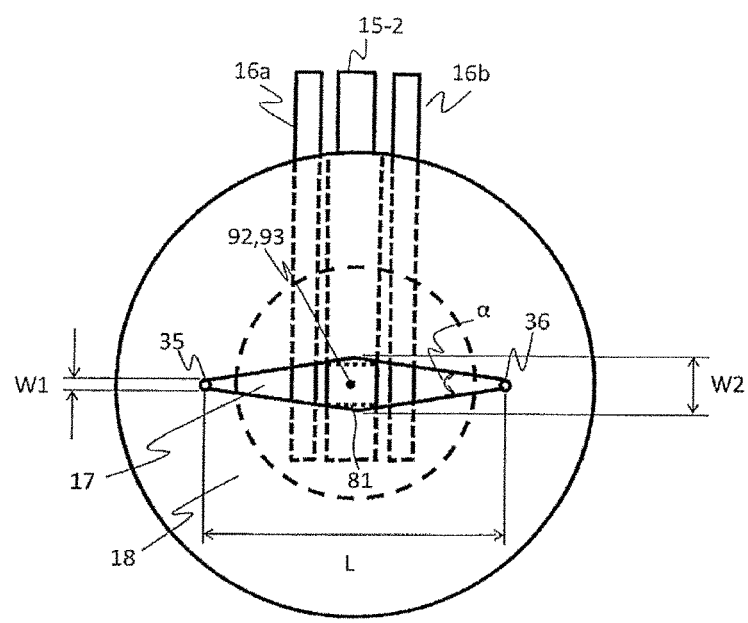
FIG. 5 is a cross-sectional view of a flow-through cell in a comparative example from a direction identical to that in FIG. 3.
Figure 6:
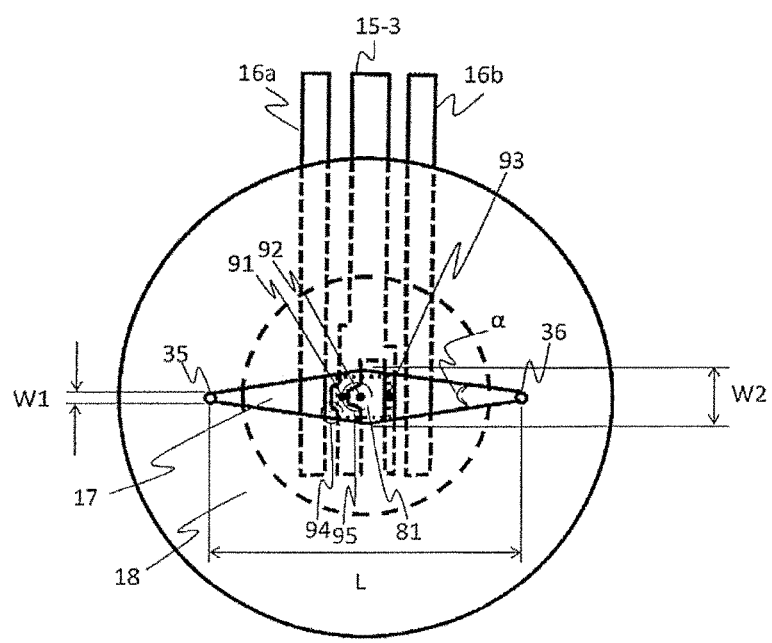
FIG. 6 is a cross-sectional view of a flow-through cell of Embodiment 2 from a direction identical to that in FIG. 3.

FIG. 1 is a diagram illustrating an overall schematic configuration of an immunity analyzing device according to an embodiment of the present invention. FIG. 2 is a longitudinal cross-sectional view illustrating a configuration of a flow-through cell unit in the device shown in FIG. 1. FIG. 3 is an enlarged view of a line III-III portion of the flow-through cell unit in FIG. 2. FIG. 4 is a cross-sectional view along a line IV-IV in FIG. 3. FIG. 5 is a cross-sectional view of a flow-through cell in a comparative example from a direction identical to that in FIG. 3. FIG. 6 is a cross-sectional view of the flow-through cell of Embodiment 2 from a direction identical to that in FIG. 3. FIG. 7 is a table that compares amounts of luminescence (arbitrary unit) of a buffer solution (corresponding to signal) including TSH and a buffer solution (corresponding to noise) including a substance (TPA) that does not include TSH and induces excitation of a labeling substance between comparative example 1, Embodiment 1 and Embodiment 2. Next, the present invention will be described more specifically using embodiments.

Embodiment 1

Hereinafter, a method and an device for immunity analysis according to an embodiment of the present invention will be described using FIG. 1 to FIG. 4. First, a system configuration of an analyzing device of the present embodiment will be described using FIG. 1.

In FIG. 1, the analyzing device of the present embodiment is provided with a sample bottle 31 containing a sample, a beads bottle 32 containing a beads solution including magnetic particles, a first reagent bottle 33 containing a first reagent that binds magnetic particles to a specific component in the sample, a second reagent bottle 34 containing a second reagent that labels a labeling substance that generates luminescence through an electrochemical reaction and is bound to a specific component in the sample, a buffer solution bottle 3 containing a buffer solution including a substance that induces electrochemical luminescence of the labeling substance, a cleaning liquid bottle 4 containing a cleaning liquid, a vessel (reactor vessel) 1 for obtaining a suspension including a reaction product, a sampling probe 30 that dispenses the sample, beads, first reagent, second reagent and buffer solution to the vessel 1, a shipper probe 2 that feeds the suspension of the vessel 1, a cleaning tank 5 that cleans a distal end portion of the shipper probe 2, a flow-through cell unit 10 into which the suspension fed from the shipper probe 2 is introduced, a syringe 11 that suctions and discharges the suspension, cleaning liquid and buffer solution, a waste liquid bottle 13 that accommodates a waste liquid, a distilled water bottle 14 that accommodates distilled water and a pump 12 that feeds the distilled water of the distilled water bottle 14 to the cleaning tank 5.

The sampling probe 30 has a known pipetting mechanism and is connected to a syringe (not shown) via a channel P1. The shipper probe 2 is connected to the flow-through cell unit 10 via a channel P2. The flow-through cell unit 10 is connected to the syringe 11 via a channel P3, a first pinch valve 7 and a channel P4. Furthermore, the channel P4 is connected to the waste liquid bottle 13 via a channel P5, a second pinch valve 8, and a channel P6. On the other hand, the distilled water bottle 14 is connected to the cleaning tank 5 via a channel P9, the pump 12 and a channel P10, and the cleaning tank 5 is connected to the waste liquid bottle 13 via a channel P11. Furthermore, a channel P8 is branched at some midpoint from the channel P10 and this channel P8 is connected to the syringe 11 via a third pinch valve 9 and a channel P7.

The sample in the sample bottle 31 is, for example, a sample originating from a biological liquid such as serum, urine containing TSH (thyroid gland hormone) which is a specific component. The beads solution in the beads bottle 32 corresponds to beads which are particulate magnetic substances embedded in a matrix of polystyrene or the like, that is, magnetic particles (specific gravity of 1.4, average particle size of 2.8 µm) scattered in a buffering liquid, and a streptavidin that can be bound to biotin is bound to the surface of this matrix. As the magnetic particles, a plurality of particulate magnetic substances contained in the matrix may be used.

The first reagent in the first reagent bottle 33 includes a TSH antibody whose end is subjected to biotin processing. The second reagent in the second reagent bottle 34 includes a TSH antibody whose end is subjected to biotin processing and to which a labeling substance causing chemical luminescence by excitation is bound. The present embodiment uses, for example, Ru(bpy)$_3$, that is, ruthenium (II) tris (bipyridyl) as the labeling substance. Ru(bpy)$_3$ exists in the form of Ru(bpy)$_3^{2+}$ in a buffer solution. The buffer solution in the buffer solution bottle 3 is reduced by application of a voltage and includes a substance inducing excitation of the labeling substance and has a pH of around 7.4. The present embodiment uses tri-propylamine (TPA) as the attractant.

Next, a structure of the flow-through cell unit will be described using FIG. 2 to FIG. 4.

The flow-through cell unit 10 includes a cell substrate 18, a PMT case 21 that houses a photoelectron multiplier 19 and a light-receiving window 22 located between the cell substrate 18 and the PMT case 21, the cell substrate 18 and the light-receiving window 22 are integrated via a spacer 18A and a flow chamber 17 through which a suspension containing the reaction product introduced into the flow-through cell unit 10 flows is formed. Note that in the present specification, a member made up of the light-receiving window 22, spacer 18A, cell substrate 18, flow chamber 17, sheet member 18b, working electrode 15, counter electrodes 16a and 16b, channel inlet 35, channel outlet 36, and nipples 50 and 51 or the like is called a "flow-through cell 6." The flow chamber 17 has a spindle shape when seen from above as shown in FIG. 4, the channel inlet 35 is located at one end of the spindle shape, the channel outlet 36 is located at the other end, and the channel inlet 35 and the channel outlet 36 are connected to the channels P2 and P3 via the nipples 50 and 51 respectively attached to the cell substrate 18. The working electrode 15 is placed in the center on the undersurface of the spindle-shaped maximum width portion of the flow chamber 17, and a pair of counter electrodes 16a and 16b are arranged on the same plane on both sides of the working electrode 15 in a symmetric form. The working electrode 15 and the counter electrodes 16a and 16b are attached to the sheet member 18B provided on the cell substrate 18, one end of which extends outside the cell substrate 18 and is connected to a power supply and a control device (not shown). A magnet 24 is located below the working electrode 15 and the magnet 24 is placed in an emarginated part 18C formed in the cell substrate 18 so as to be able to approach the working electrode 15. The magnet 24 is attached to a magnet holder 25 and the magnet holder 25 is attached to one end of a lever 25A. The other end of the lever 25A is attached to a stepping motor 26, is pivotable around a fulcrum 28, and the magnet 24 can go in and out between an illustrated working position in the concave part 18C and a retracted position shown by a two-dot dashed line outside the emarginated part 18C by operating the stepping motor 26.

The photoelectron multiplier 19 is intended to measure light which is generated in the flow chamber 17 and passes through the light-receiving window 22, and R1878 manufactured by Hamamatsu Photonics K.K. is used here. The photoelectron multiplier 19 is housed in the PMT case 21 which is covered with a shield tube 20 to prevent deterioration of multiplication efficiency by magnetism. A socket 27 is attached above the photoelectron multiplier 19, a detection signal of the photoelectron multiplier 19 is sent to a control device (not shown) via the socket 27 whereby light intensity is measured.

The spacer 18A that forms a side face of the flow chamber 17 and a sheet member 18B that forms an undersurface are made of polytetrafluoroethylene. Furthermore, in the flow chamber 17, a minimum width W1 at both ends of the spindle shape is 1 mm, a maximum width W2 in the center is 5 mm, a flow chamber length L in the center is 33 mm, an angle of aperture α is 16.2°, and a thickness t is 0.5 mm. The diameters of the channel inlet 35 and the channel outlet 36 of the flow chamber 17 are equal to the minimum width W1, that is, 1 mm.

The working electrode 15 is made of platinum, and in the region where the working electrode 15 is exposed in the flow chamber as shown in FIG. 3 and FIG. 4 forms a trapezoid having an upper side length of 4.1 mm, a lower side length of 5 mm, a height (width) of 3 mm, and an area of approximately 13.6 mm$^2$.

The counter electrodes 16 are also made of platinum as with the working electrode 15 and are arranged at a distance of 2 mm from the working electrode 15.

The plane of the magnet 24 facing the flow chamber 17 is a rectangle of 4.6 mm×5 mm and has an area of 23 mm$^2$. Therefore, the area of the region where the working electrode is exposed in the flow chamber is smaller than the area of the top part of the magnet and the ratio of the former to the latter is 13.6/23=59% (⅔ or less). To set the ratio of the former to the latter to ⅓ or less, for example, the height (width) of the trapezoidal region where the working electrode is exposed in the flow chamber may be set to 1.5 mm. Moreover, a centroid 91 of the region where the working electrode is exposed in the flow chamber is located closer to the upstream side of the flow than a centroid 92 of the top part of the magnet. Note that since this flow flows from the channel inlet 35 to the channel outlet 36, a position closer to the channel inlet 35 corresponds to the upstream side.

Furthermore, the magnet is a permanent magnet, the working electrode 15 side thereof is magnetized to an N pole and has a magnetic flux density of 0.85 T. The magnet 24 is placed at a distance of 1 mm from the surface of the working electrode 15 in the working position in the emarginated part 18C. The light-receiving window 22 is made of acrylic which is a non-conductive plastic material having a light transmissivity of 90% or higher and is shaped like a disk having a thickness of 4 mm, and an effective diameter of 25 mm.

Next, operation of the immunity analyzing device according to the present embodiment configured as described above will be described.

A sample 50 μl originating from a biological liquid such as serum, urine including TSH (thyroid gland stimulating hormone) which is a specific component in the sample bottle 31, a beads solution 50 μl scattered in the buffer solution in the beads bottle 32, a first reagent 50 μl including the TSH antibody which is an end in the first reagent bottle 33 subjected to biotin processing, a second reagent 50 μl including the TSH antibody which is an end in the second reagent bottle 34 subjected to biotin processing and to which the labeling substance producing chemical luminescence through excitation is bound, and a buffer solution 50 μl having a pH of around 7.4 including the attractant in the buffer solution bottle 3 are dispensed into the vessel 1 in a predetermined sequence by the sampling probe 30. Here, since a sandwich method is used for analysis, the beads solution, first reagent, sample and second reagent are dispensed in that order.

During the dispensation operation, the inside of the vessel 1 is stirred by a vibration device (not shown) while keeping it to a constant temperature (37° C. in the present embodiment), causing a reaction to advance, and heat insulation and stirring are continued for a predetermined time (15 minutes in the present embodiment) after the dispensation operation. Thus, a suspension is generated which includes a reaction product in which the magnetic particles, first reagent, TSH in the sample and second reagent are bound in the vessel 1.

Next, the suspension in the vessel 1 is introduced into the flow chamber 17 of the flow-through cell unit 10. This operation is performed as follows. First, in FIG. 2, the stepping motor 26 is driven to move the magnet 24 to the working position shown by a solid line in FIG. 2. Next, in FIG. 1, the first pinch valve 7 is opened and the second pinch valve 8 and the third pinch valve 9 are closed. In this condition, the shipper probe 2 is horizontally moved above the vessel 1 by a drive device (not shown), then moved downward and the distal end portion thereof is inserted into the suspension in the vessel 1.

Next, 200 µl out of 250 µl of the suspension containing the reaction product in the vessel 1 is suctioned into the shipper probe 2 by the syringe 11, the shipper probe 2 is then moved upward, the distal end portion thereof is caused to go out of the suspension, and the suspension in the shipper probe 2 is suctioned by the syringe 11 again. This suction causes 200 µl of the suspension to be introduced into the flow-through cell unit 10 via the channel P2 and to flow through the flow chamber 17. In this case, the operation of the syringe 11 is controlled so that the suspension flows through the flow chamber 17 from the channel inlet 35 at a linear velocity of 50 mm/s. When the suspension reaches the working electrode 15, only the reaction product and unreacted magnetic particles are trapped on the working electrode 15 through a magnetic field locally formed by the magnet 24 and the other unreacted first reagent and second reagent are suctioned into the syringe 11 after passing through the flow chamber 17. By this means, all the reaction products included in the 200 µl of suspension are gathered into the flow chamber 17 where B/F separation is performed.

Next, the shipper probe 2 is horizontally moved above the cleaning tank 5, then moved downward, and the distal end portion thereof is located in the cleaning tank 5, and the pump 12 is driven in this condition, distilled water in the distilled water bottle 14 is discharged into the cleaning tank 5 via the channel P9, pump 12 and channel P10 and the outside of the distal end portion of the shipper probe 2 is thereby cleaned. The used distilled water discharged into the cleaning tank 5 is sent as a waste liquid from the bottom of the cleaning tank 5 to the waste liquid bottle 13 via the channel P11.

Next, the shipper probe 2 is moved upward, the distal end portion thereof is caused to go out of the cleaning tank 5, horizontally moved above the buffer solution bottle 3, the shipper probe 2 is further moved downward, and the distal end portion thereof is inserted into a buffer solution in the buffer solution bottle 3. Next, the buffer solution in the buffer solution bottle 3 is suctioned by the syringe 11 and 1000 µl of the buffer solution is introduced into the flow-through cell unit 10. The introduction of the buffer solution causes an unreacted second reagent remaining in the flow chamber 17 of the flow-through cell unit 10 to be washed away, completing B/F separation. In this case, the buffer solution used for cleaning and the unreacted reagent are inhaled into the syringe 11 from the flow chamber 17 via the channel P3, first pinch valve 7 and channel P4.

In the flow chamber 17, the reaction product and the unreacted first reagent (magnetic particles) are trapped on the working electrode 15 through the above-described operation and the periphery thereof, that is, the whole flow chamber 17 is filled with a buffer solution containing TPA used to induce excitation of the labeling substance. On the other hand, the buffer solution and the unreacted reagent suctioned into the syringe 11 are discharged into the waste liquid bottle 13 by the syringe 11 by closing the first pinch valve 7 and then opening the second pinch valve 8.

After completion of the above-described process, a voltage based on a predetermined sequence is applied between the working electrode 15 and the counter electrodes 16 arranged on both sides thereof on the same plane and the following reaction is caused to take place.

1) $TPA \rightarrow TPA^+ + e^-$
2) $TPA^+ \rightarrow TPA^* + H^+$
3) $Ru(bpy)_3^{2+} \rightarrow Ru(bpy)_3^{3+} + e^-$
4) $Ru(bpy)_3^{3+} + TPA^* \rightarrow Ru(bpy)_3^{2+*}$
5) $Ru(bpy)_3^{2+*} \rightarrow Ru(bpy)_3^{2+} + photon$ (620 nm)

That is, TPA in the buffer solution is reduced with the application of a voltage and $Ru(bpy)_3^{2+}$ which is the labeling substance in the reaction product emits light. The light generated by this reaction is introduced onto the photoelectric plane of the photoelectron multiplier 19 via the transparent light-receiving window 22 provided on the flow chamber 17, the amount of luminescence is measured and a TSH concentration in the sample is calculated in comparison with the amount of luminescence when a control substance whose TSH concentration is known is measured.

In the above-described reaction process, the magnet 24 arranged on the working electrode 15 for the purpose of trapping a reaction product which is bound to magnetic particles is moved to a retracted position where the plane of the working electrode 15 is not affected by the magnetic field by driving the stepping motor 28 immediately before or, if possible, immediately after carrying out luminescence through electrochemical reaction by application of a voltage to reduce influences of the magnetic field on the multiplication efficiency of the photoelectron multiplier tube.

After completion of luminescent reaction, the inside of the flow chamber 17 is cleaned. First, the first pinch valve 7 is opened, the second pinch valve 8 and the third pinch valve 9 are closed, the shipper probe 2 whose distal end is cleaned with distilled water beforehand is horizontally moved above the cleaning liquid bottle 4 as described above, then moved downward, the distal end portion thereof is inserted into the cleaning liquid in the cleaning liquid bottle 4, and suction of the cleaning liquid in the cleaning liquid bottle 4 is started by the syringe 11. In this case, it is preferable to move the shipper probe 2 upward and downward while suctioning the cleaning liquid by the syringe 11 and suction the cleaning liquid and air by a predetermined amount at a time for the purpose of improving cleaning efficiency. The cleaning liquid suctioned in this way is guided into the flow chamber 17 in the flow-through cell unit 10 via the channel P2 to wash away the buffer solution remaining in the flow chamber 17 after completion of reaction, and the reaction product and unreacted first reagent (magnetic particles). After this, the waste liquid and cleaning liquid suctioned into the syringe 11 are discharged into the waste liquid bottle 13 by closing the first pinch valve 7, opening the second pinch valve 8 and pressing the syringe 11.

After an end of the above-described process, the second pinch valve 8 is closed again, the first pinch valve 7 is opened, 1000 µl of the buffer solution containing TPA is suctioned from the inside of the buffer solution bottle 3 by the shipper probe 2 whose distal end is cleaned with distilled water beforehand using the syringe 11, the cleaning liquid remaining in the channel P2 and the flow chamber 17 of the flow-through cell unit 10 is washed away, and the inside of the channel P2 and the flow chamber 17 is substituted by the buffer solution. Measurement of TSH corresponding to one sample is completed through this operation.

In order to study an improvement of the actual SN ratio through the above-described operation and using the flow-through cell 6, a buffer solution (concentration: 1 uIU/ml) containing TSH as one corresponding to a signal and a buffer solution not containing TSH and containing a substance (TPA) that induces excitation of the labeling substance as one corresponding to noise are measured respectively and their amounts of luminescence (arbitrary unit) are compared. Table 1 shows the results.

TABLE 1

|  | Signal: TSH concentration = 1 uIU/ml | Noise: TPA containing buffer solution, TSH concentration = 0 uIU/ml | Signal/ Noise |
|---|---|---|---|
| Comparison 1 | 7962 | 1007 | 7.9 |
| Embodiment 1 | 4152 | 351 | 11.8 |
| Embodiment 2 | 6097 | 421 | 14.5 |

Table 1 also shows a measurement result in a case using a flow-through cell whose working electrode has a shape shown in FIG. 5 as comparison 1. The area of an exposed region in the flow chamber of a working electrode 15-2 shown in FIG. 5 is substantially equal to that of the top part of the magnet and is approximately 23.1 mm$^2$. The rest of the configuration is similar to that in FIG. 4. Therefore, the area of the exposed region of the working electrode in the flow chamber is slightly larger than the area of the top part of the magnet and the ratio of the former to the latter is 23.1/23>100%. Furthermore, the centroid 91 of the exposed region of the working electrode in the flow chamber coincides with the centroid 92 of the top part of the magnet.

As is clear from Table 1, present Embodiment 1 has a higher SN ratio (Signal/Noise in Table 1) than that in comparison 1. This may be attributable to the fact that since the working electrode is selectively arranged in the region where magnetic particles are trapped, it is possible to improve the ratio of luminescence of the luminescence attractant with respect to the ratio of luminescence from a target luminescent label originating from TSH.

Embodiment 2

FIG. 6 illustrates another embodiment of the present invention.

A flow-through cell configuration thereof is similar to that of the flow-through cell created in Embodiment 1 except the working electrode shape. A working electrode 15-3 is bifurcated in an exposed region where the working electrode in the flow chamber. The exposed region on the upstream side of the flow chamber is called an "upstream-side working electrode exposed region" and the exposed region on the downstream side is called a "downstream-side working electrode exposed region."

The upstream-side working electrode exposed region includes upstream-side emarginated parts 94 at both ends on the upstream side thereof. On the other hand, the upstream-side working electrode exposed region includes a downstream-side emarginated part 95 on the downstream side thereof. A centroid 91-3 of the upstream-side working electrode exposed region is located in the upstream side from the centroid 92 of the top part of the magnet, and a centroid 93 of the downstream-side working electrode exposed region is located in the downstream side from the centroid 92 of the top part of the magnet.

The area of the exposed region of the working electrode 15-3 in the flow chamber shown in FIG. 6 which includes both the upstream-side working electrode exposed region and the downstream-side working electrode exposed region is 14.5 mm$^2$. Therefore, the area of the exposed region of the working electrode in the flow chamber is smaller than the area of the top part of the magnet and the ratio of the former to the latter is 14.5/23=63% (smaller than ⅔).

As is clear from Table 1, it is seen that present Embodiment 2 has a higher SN ratio than that of comparison 1 or moreover Embodiment 1. This may be attributable to the fact that causing the working electrode to have a shape closer to the region in which magnetic particles are trapped can increase the ratio of luminescence of the luminescent attractant with respect to the ratio of luminescence from a target luminescent label originating from TSH.

Embodiment 3

Another embodiment of the present invention will be described.

The present embodiment assumes that the working electrode has a shape similar to a conventional one. The light-receiving window 22 is partially covered to prevent luminescence generated from the downstream side of the trapping region from entering the photomultiplier tube. This prevents luminescence from regions where there are numerous noise components from entering the photomultiplier tube, leading to an improvement of the SN ratio. Moreover, covering the light-receiving window eliminates the necessity for fine processing/control of the electrode shape (may also be a shape identical to or simpler than that of the comparative example). Therefore, it is possible to reduce variations in electrochemical reaction efficiency originating from variations in the working accuracy of the electrode end or the like when working the electrode shape. That is, it is possible to improve the SN ratio without causing the accuracy of the flow-through cell or analyzing device to deteriorate.

REFERENCE SIGNS LIST

1 Vessel
2 Shipper probe
3 Buffer solution bottle
4 Cleaning liquid bottle
5 Cleaning tank
6 Flow-through cell
7 First pinch valve
8 Second pinch valve
9 Third pinch valve
10 Flow-through cell unit
11 Syringe
12 Pump
13 Waste liquid bottle
14 Distilled water bottle
15 Working electrode
16a, 16b Counter electrode
17 Flow chamber
18 Cell substrate
18a Spacer
18b Sheet member
18c Emarginated part
19 Photomultiplier tube
20 Shield tube
21 PMT case
22 Light-receiving window 24 Magnet
25 Magnet holder
25A Lever
26 Stepping motor
27 Socket
28 Fulcrum
30 Sampling probe
31 Sample bottle
32 Beads bottle
33 First reagent bottle
34 Second reagent bottle
35 Channel inlet
36 Channel outlet
50, 51 Nipple
81 Region corresponding to top part of magnet
91 Centroid of exposed region in flow chamber of working electrode
91-3 Centroid of upstream-side working electrode exposed region
92 Centroid of top part of magnet
93 Centroid of downstream-side working electrode exposed region
94 Upstream-side emarginated part
95 Downstream-side emarginated part

The invention claimed is:

1. An analyzing device comprising:
 a flow chamber that a fluid having magnetic particles associated with a labeling substance flows from a fluid inlet to a fluid outlet;
 a magnetic trap means for trapping the magnetic particles from the fluid in said flow chamber, wherein the magnetic trap means comprises a magnet to apply a magnetic field;
 a working electrode and a counter electrode to apply a voltage to the magnetic particles trapped by said magnetic trap means, and to emit a luminescence;
 a light detection element to detect a luminescence derived from the labeling substance on the magnetic particles trapped in said flow chamber; and
 wherein the working electrode is arranged to be exposed to an upstream part of and closer to the fluid inlet than an internal surface of the flow chamber on which the magnetic particles are trapped by said magnetic trap means, and
 wherein a total area of said working electrode in the flow chamber is less than a total area of a top part of said magnetic trap means which faces the flow chamber.

2. The analyzing device of claim 1, wherein the total area of said working electrode in the flow chamber is equal to or less than ⅓ of the total area of the top part of said magnetic trap means which faces the flow chamber.

3. The analyzing device of claim 1 wherein a centroid of said working electrode in the flow chamber is located in an upstream side of said flow chamber inside from a centroid of the top part of said magnetic trap means which faces the flow chamber.

4. The analyzing device of claim 1, wherein a figuration of an exposed part of said working electrode is formed emarginately in a downstream side of the flow chamber.

5. The analyzing device of claim 1, wherein a figuration of an exposed part of said working electrode is formed emarginately in near a sidewall of an upstream side of the flow chamber.

6. The analyzing device of claim 1, wherein the total area of said working electrode in the flow chamber is equal to or less than ⅔ of the total area of the top part of said magnetic trap means which faces the flow chamber.

7. The analyzing device of claim 1, wherein the working electrode and the counter electrode in the flow chamber are arranged on a plane that extends from the fluid inlet to the fluid outlet.

8. A flow-through cell comprises:
 a fluid inlet where a fluid having magnetic particles associated with a labeling substance is flowed into;
 a fluid outlet where said fluid is exhausted from;
 a trapping region for trapping the flowed magnetic particles;
 a working electrode and a counter electrode to apply a voltage to the magnetic particles trapped by a magnetic trap means, wherein the magnetic trap means comprises a magnet to apply a magnetic field, and to emit a luminescence;
 a window arranged opposed to said trapping region, and passing a luminescence from the labeling substance; and
 wherein the working electrode is arranged to be exposed to an upstream part of and closer to the fluid inlet than said trapping region in which the magnetic particles are trapped by said magnetic trap means, and
 wherein a total area of said working electrode in the flow chamber is less than a total area of a top part of said magnetic trap means which faces the flow chamber.

9. The flow-through cell of claim 8, wherein the total area of said working electrode in the flow chamber is equal to or less than ⅓ of the total area of the top part of said magnetic trap means which faces the flow chamber.

10. The flow-through cell of claim 8, wherein a centroid of said working electrode in the flow chamber is located upstream from a centroid of said trapping region.

11. The flow-through cell of claim 8, wherein a figuration of an exposed part of said working electrode is formed emarginately in a downstream side of said trapping region.

12. The flow-through cell of claim 8, wherein a figuration of an exposed part of said working electrode is formed emarginately in near a sidewall of an upstream fluid passage.

13. The flow-through cell of claim 8, wherein the total area of said working electrode in the flow chamber is equal to or less than ⅔ of the total area of the top part of said magnetic trap means which faces the flow chamber.

14. The flow-through cell of claim 8, wherein the working electrode and the counter electrode in the flow chamber are arranged on a plane that extends from the fluid inlet to the fluid outlet.

15. An analyzing device comprising:
 a flow chamber that a fluid having magnetic particles associated with a labeling substance flows from a fluid inlet to a fluid outlet;
 a magnetic trap means for trapping the magnetic particles from the fluid in said flow chamber, wherein the magnetic trap means comprises a magnet to apply a magnetic field;
 a working electrode and a counter electrode to apply a voltage to the magnetic particles trapped by said magnetic trap means, and thereby cause a luminescence from the labeling substance to emit;
 a light detection element to detect the luminescence emitted from the labeling substance on the magnetic particles trapped in said flow chamber; and
 a window for passing the luminescence emitted from the labeling substance, wherein the luminescence passing said window regulates to the luminescence emitted from the labeling substance on upstream ones of the magnetic particles trapped by said magnetic trap means, wherein the working electrode is arranged to be exposed to an upstream part of and closer to the fluid inlet than an internal surface of the flow chamber on which the magnetic particles are trapped by said magnetic trap means, and wherein a total area of said working electrode in the flow chamber is less than a total area of a top part of said magnetic trap means which faces the flow chamber.

16. A flow-through cell comprises:
a fluid inlet where a fluid having magnetic particles associated with a labeling substance is flowed into;
a fluid outlet where said fluid is exhausted from;
a trapping region for trapping the flowed magnetic particles;
a working electrode and a counter electrode to apply a voltage to the magnetic particles trapped by a magnetic trap means, wherein the magnetic trap means comprises a magnet to apply a magnetic field, and thereby cause a luminescence from the labeling substance to emit; and
a window arranged opposed to said trapping region and which passes the luminescence emitted from the labeling substance, wherein the luminescence passing said window regulates to the luminescence from the labeling substance on upstream ones of the magnetic particles trapped in said trapping region, wherein the working electrode is arranged to be exposed to an upstream part of and closer to the fluid inlet than said trapping region in which the magnetic particles are trapped by said magnetic trap means, and wherein a total area of said working electrode in the flow chamber is less than a total area of a top part of said magnetic trap means which faces the flow chamber.

* * * * *